US00PP25310P3

(12) United States Plant Patent
Strode

(10) Patent No.: US PP25,310 P3
(45) Date of Patent: Feb. 24, 2015

(54) *ALOCASIA* PLANT NAMED 'MANDALAY'

(50) Latin Name: *Alocasia amazonica*
Varietal Denomination: Mandalay

(71) Applicant: Agri-Starts, Inc., Apopka, FL (US)

(72) Inventor: Ty Richard Strode, Apopka, FL (US)

(73) Assignee: Agri-Starts, Inc., Apopka, FL (US)

( * ) Notice: Subject to any disclaimer, the term of this patent is extended or adjusted under 35 U.S.C. 154(b) by 1 day.

(21) Appl. No.: 13/986,303

(22) Filed: Apr. 19, 2013

(65) Prior Publication Data

US 2013/0239277 P1 Sep. 12, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

PUBLICATIONS

AgriStarts, obtained online Jun. 15, 2014.*
*Alocasias* Database, obtained online Jun. 15, 2014.*

* cited by examiner

*Primary Examiner* — June Hwu
*Assistant Examiner* — Keith Robinson
(74) *Attorney, Agent, or Firm* — Jondle & Associates, P.C.

(57) ABSTRACT

A new and distinct variety of *Alocasia* plant named 'Mandalay' particularly characterized by a short, compact growing plant having ovate leaves with pronounced silver venation is disclosed.

4 Drawing Sheets

Genus and species: *Alocasia amazonica.*
Variety denomination: 'Mandalay'.

BACKGROUND OF THE NEW PLANT

The present invention comprises a new and distinct variety of *Alocasia* plant, botanically known as *Alocasia amazonica* and hereinafter referred to by the variety name 'Mandalay'. The new variety was discovered on Mar. 9, 2011 in Apopka, Fla. as a naturally-occurring whole plant mutation of *Alocasia amazonica* c.v. 'Polly' (unpatented) within a nursery shipment of 'Polly'. A single plant selection was subsequently chosen for further evaluation and asexual propagation.

'Mandalay' was first propagated via tissue culture in Apopka, Fla. in June of 2011 and has been asexually reproduced by tissue culture in Apopka, Fla. for approximately 14 generations. 'Mandalay' has been found to retain its distinctive characteristics through successive asexual propagations via tissue culture.

Plant Breeder's Rights for this variety have not been applied for. 'Mandalay' has not been sold or made publicly available anywhere in the world more than one year prior to the filing date of this application.

SUMMARY OF THE INVENTION

The following are the most outstanding and distinguishing characteristic of this new variety when grown under normal horticultural practices in a greenhouse in Apopka, Fla.

1. Short, compact growing plant; and
2. Sagittate leaves with pronounced silver venation.

DESCRIPTION OF THE PHOTOGRAPHS

This new *Alocasia* plant is illustrated by the accompanying photographs; the colors shown are as true as can be reasonably obtained by conventional photographic procedures. The photographs are of a whole plant about 35 weeks old.

DESCRIPTION OF THE NEW VARIETY

Figure 1:
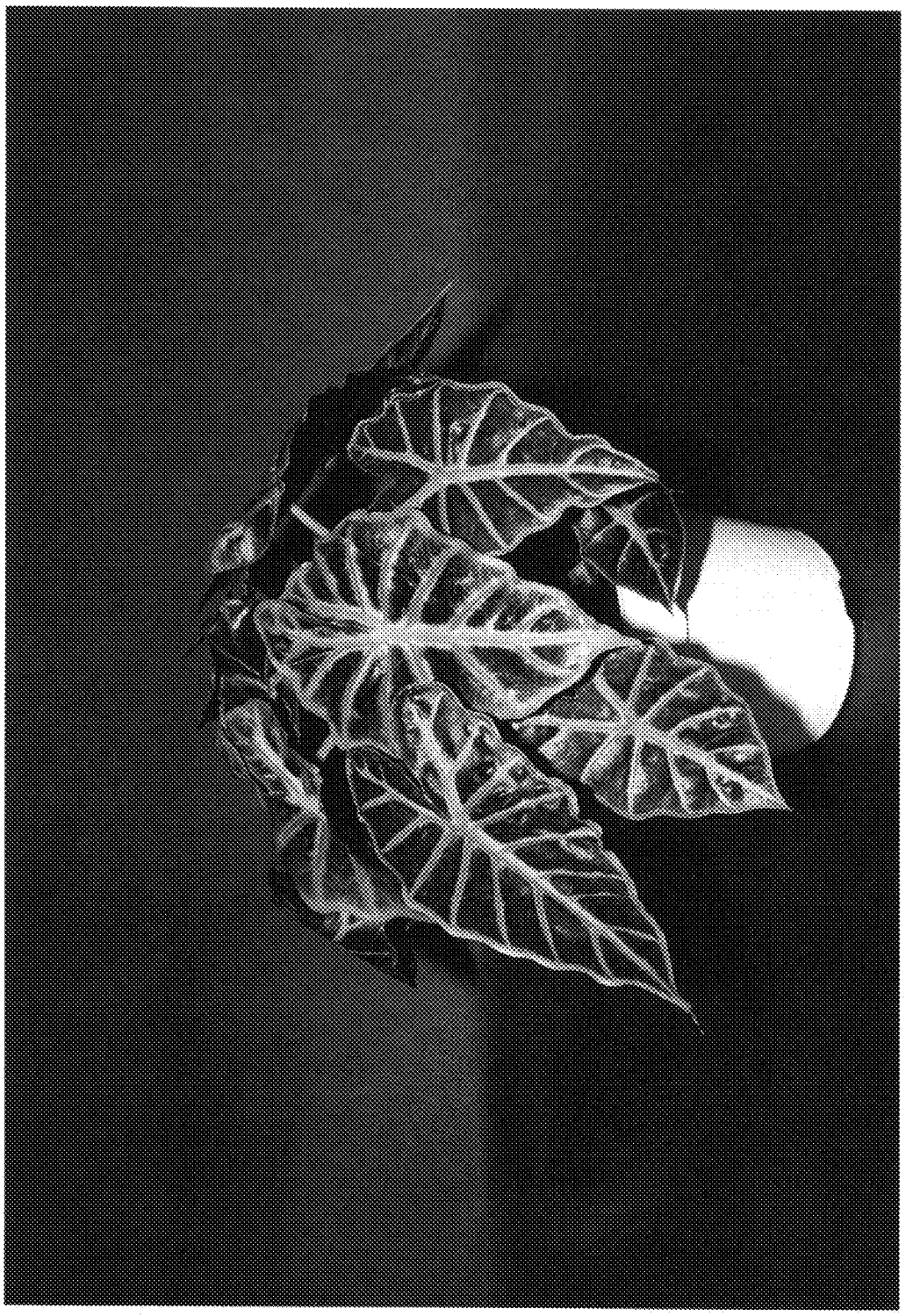
FIG. 1 shows a whole plant of 'Mandalay' in a 6 inch pot.
Figure 2:
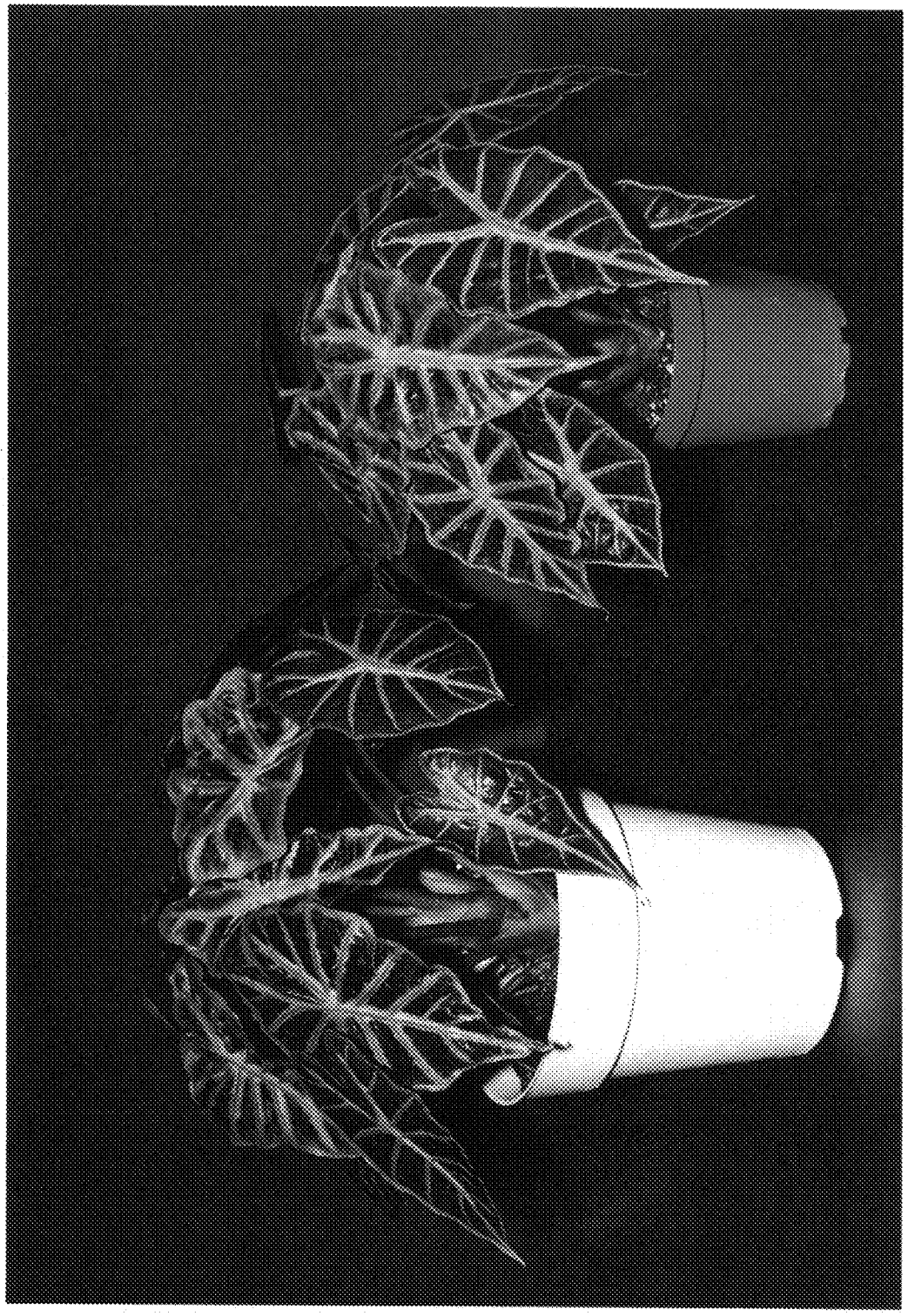
FIG. 2 shows whole plants of 'Mandalay' in 6 inch and 4 inch pots.
Figure 3:
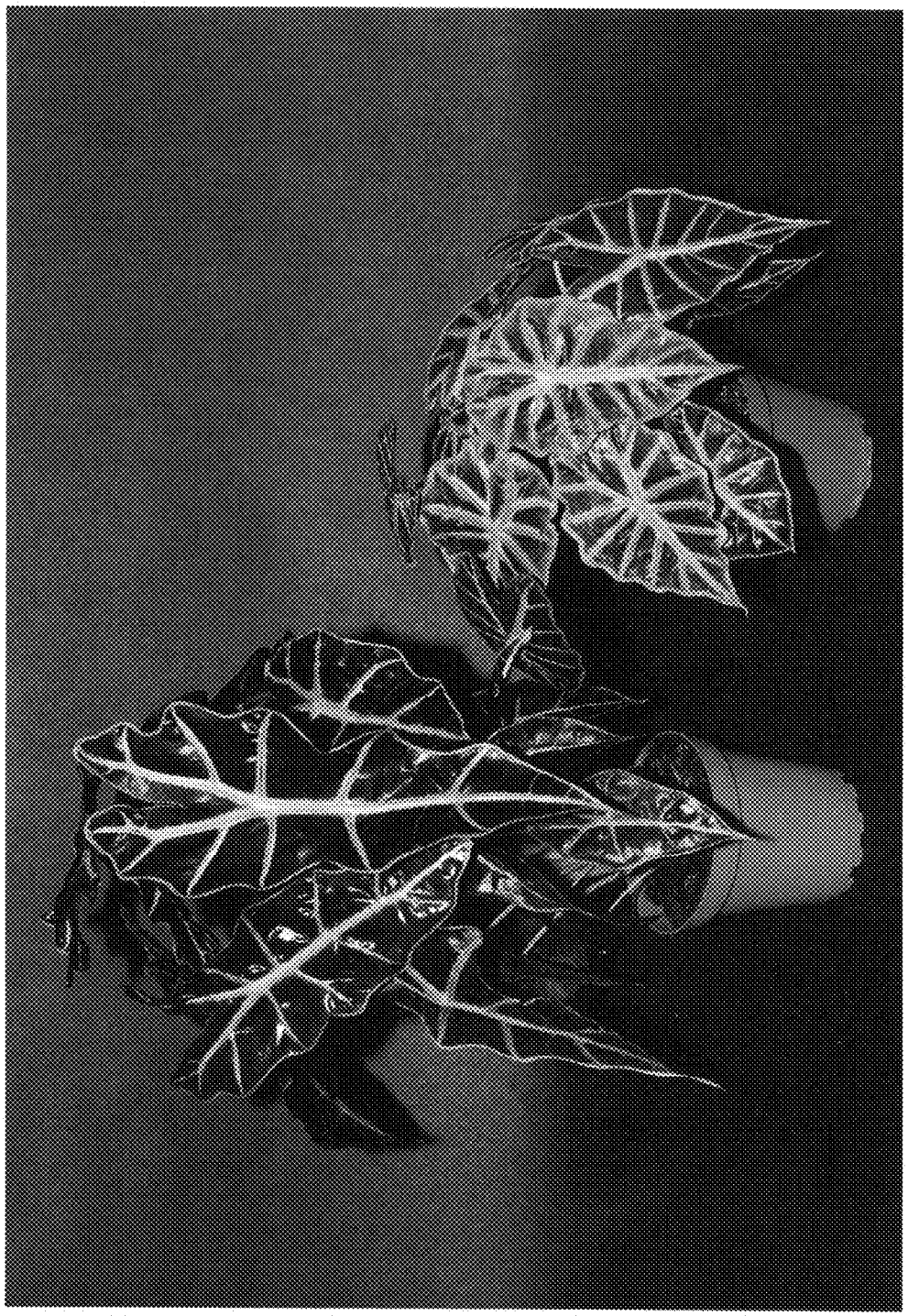
FIG. 3 shows the parent plant 'Polly' on the left and 'Mandalay' on the right in a 6 inch pot.
Figure 4:
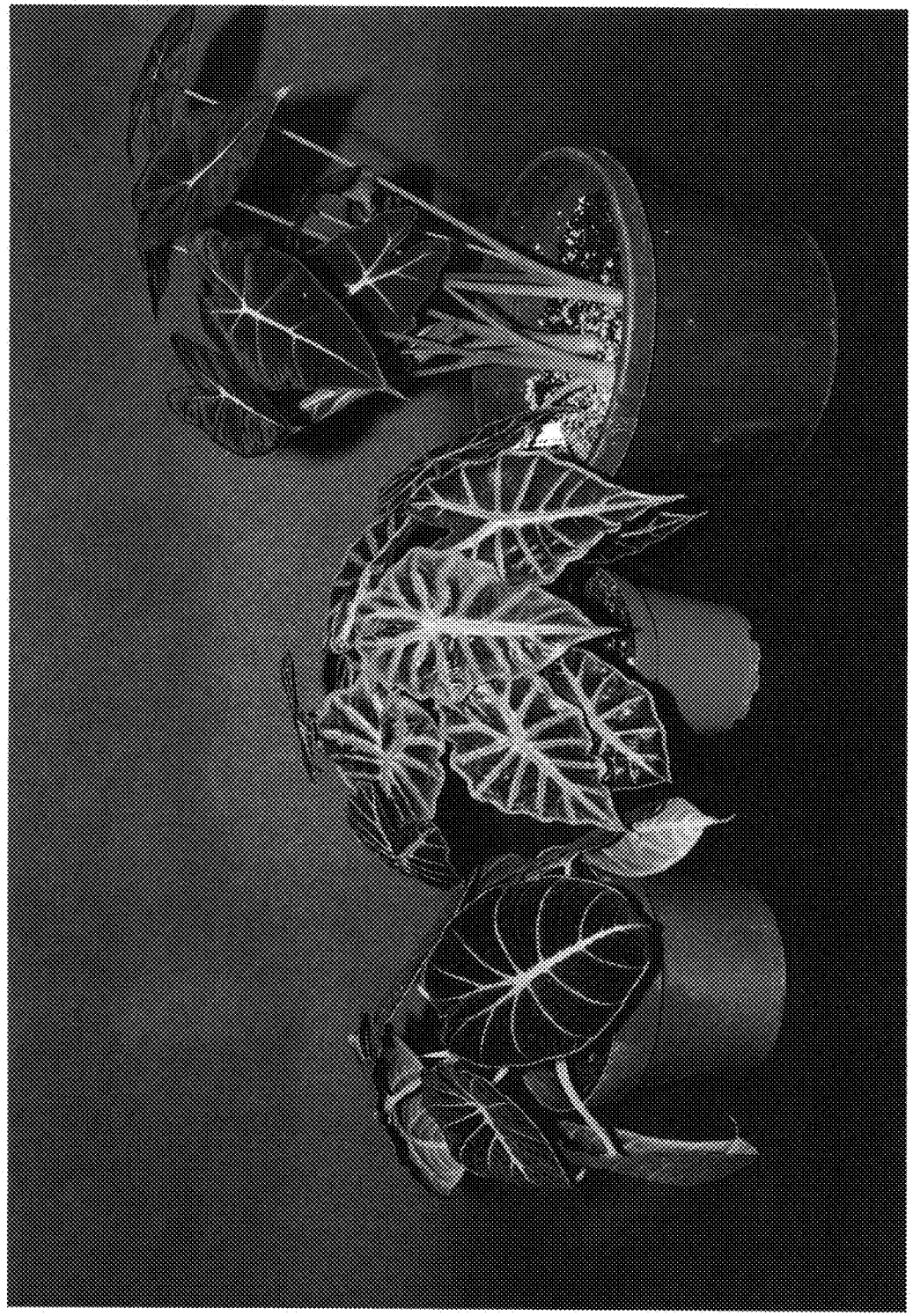
FIG. 4 shows comparison variety *Alocasia* 'Black Velvet' (unpatented) on the left, 'Mandalay' in the middle, and comparison variety *Alocasia* 'Frydek' (unpatented) on the right.

The following detailed description sets forth the distinctive characteristics of *Alocasia* 'Mandalay'. The data which define these characteristics was collected from asexual reproductions carried out in Apopka, Fla. The plant history was taken in March of 2013 on 35 week old plants grown in 15 centimeter pots. The plants were grown from a tissue culture starter plant in a controlled climate greenhouse with natural light in 50-70% shade. Color readings were taken under natural light in the greenhouse. Color references are primarily to The R.H.S. Colour Chart of The Royal Horticultural Society of London (R.H.S.) (2001 edition).

DETAILED BOTANICAL DESCRIPTION OF THE NEW PLANT

Classification:
*Family.*—Araceae.
*Botanical.*—*Alocasia amazonica.*
*Common.*—*Alocasia.*

Parentage:
*Parent.*—Naturally occurring whole plant mutation of *Alocasia amazonica* c.v. 'Polly'.

Plant:

*Plant type*.—Indoor plant, cultivated year round for its tropical foliage.

*Form*.—Upright, wider than tall.

*Growth and branching habit*.—Singular stem, short internodes. Leaves arranged in short vertical ranks, mounded growth habit.

*Height* (*cm*).—About 19 cm.

*Width* (*cm*).—30 cm to 37 cm.

*Time to initiate and develop roots*.—3 weeks in the summer and 4 weeks in the winter to initiate roots from a tissue culture derived micro cutting.

*Root description*.—Thick, fleshy roots, mostly un-branched with fine laterals.

*High temperature tolerance*.—Approximately 40° Celsius.

*Low temperature tolerance*.—Approximately 13° Celsius.

*How propagated* (*by cuttings, division, tissue culture*) .—Tissue culture, or cormels.

Leaves:

*Arrangement*.—Thick, short fleshy stem with closely spaced leaves in vertical ranks.

*Quantity of leaves per stem*.—Approximately 13.

*Length* (*cm*).—Juvenile leaves are 9 cm-12 cm in. Fully expanded leaves are 15.0 cm-18.5 cm in length.

*Width* (*cm*).—Juvenile leaves are 4.2 cm-5.5 cm in width. Fully expanded leaves are 9.0 cm-10.2 cm in width.

*Shape*.—Sagittate.

*Apex*.—Cuspidate while juvenile, becoming acuminate with plant maturity.

*Base*.—Sagittate-peltate.

*Margin*.—Undulate to somewhat lobed, more so with maturity.

*Texture*.—Upper surface: Mostly flat, glabrous, glossy sheen, and somewhat wavy. Lower surface: Glabrous, glossy, to somewhat shiny, and somewhat wavy.

*Immature leaf*.—Newly emerged leaves. Color: Upper surface: Greener and lighter than RHS N189A with areas of RHS 194D tinged with N189A; midrib is RHS 147C tinged with 146C; margin of leaf is RHS 194A. Lower surface: RHS N186C tinged with N186A; midrib is RHS 147D tinged with N186C.

*Mature leaf*.—Fully expanded leaves. Color: Upper surface: RHS N189A and N189 flushed with 191C; midrib is RHS 147B and RHS 147C; margin of leaf is RHS 194B. Lower surface: RHS N187A; midrib is RHS 147C with tinges of RHS N187A.

*Venation pattern* (*both immature and mature leaves*).—Upper surface: Reticulate. Lower surface: Reticulate.

*Venation color* (*immature leaf*).—Upper surface: Primary veins are RHS 147C; surrounding veins is metallic silver RHS 190D. Lower surface: Primary veins are RHS N186C; small veins are RHS 189A.

*Venation color* (*mature leaf*).—Upper surface: Primary veins are RHS 147B; surrounding veins is RHS 191D. Lower surface: Primary veins are RHS N187A with 148C; small veins are RHS 148C.

Petiole:

*Aspect*.—New leaves curve outward. Leaves arranged about 30-45 degrees from vertical axis.

*Length* (*cm*).—14 cm to 19 cm.

*Diameter* (*cm*).—The distal (below leaf) is 3.5 mm and the proximal is 6 5 mm.

*Color*.—Distal: RHS 147C-D. Proximal: RHS 147C, tinged with N199A and faintly stippled with N199B.

*Texture*.—Smooth/glossy.

*Geniculum*.—Not observed.

*Wing length*.—Approximately 4.5 cm.

*Wing diameter*.—Approximately 3.2 cm.

*Wing color*.—Inner Surface: RHS 155C with fine venation of 183D. Outer Surface: RHS 195B tinged with 159C. Also with fine venation of RHS 183B.

Cataphylls:

*Length*.—Variable with leaf size, 6.4 cm to 10.4 cm.

*Width*.—Midpoint at 2.3 cm.

*Shape*.—Triangular, wedge shaped. Somewhat translucent, colors and pattern from outside surface visible through inside surface.

*Texture*.—Smooth glossy inside, glossy to dull outside.

*Color*.—RHS 195B with fine 177A venation.

Stem:

*Number of branches per plant*.—1 main stem with approximately 9 cormels.

*Length* (*measure from soil surface to junction of the last two unrolled leaves*).—About 8.0 cm.

*Diameter*.—Spindle shaped, upright columnar, 3.0 cm in center.

*Internode length*.—Variable, 2 mm at narrowest point and 9 mm at widest point.

*Color*.—Immature: RHS N170D. Mature: RHS N170D to N170C with tinges of 147B to 147C.

*Texture*.—Smooth, glossy to shinny.

*Strength*.—Firm, inflexible.

*Axillary buds*.—Shape: Elliptic and raised. Size: 8 mm wide, 6 mm tall, and 2 mm raised. Color: Range from RHS 147B to 147A. Sheathing leaves are RHS 200D.

Cormels:

*Shape*.—Round to obovate, with a single closed shoot at the top.

*Colors*.—Immature: RHS 155D. Mature: RHS 200A to 200B and darker, but closer to 200A.

*Size*.—Smallest: 9 mm diameter and 19 mm length. Largest: 16 mm diameter and 34 mm length.

Inflorescence: Spadix.

Fruit and seed set: No fruit or seed have been observed.

Disease and insect/pest resistance: Appears slightly more resistant to *Erwinia* than other "Jewel Type" *Alocasia*.

COMPARISON WITH PARENTAL AND COMMERCIAL VARIETIES

*Alocasia* 'Mandalay' differs from the parent *Alocasia* plant 'Polly' (unpatented) by having a shorter compact growth habit, shorter more ovate leaves, and more pronounced silver markings with lighter green interveinal areas, whereas 'Polly' has a taller more upright growth habit, longer larger leaves, and less pronounced silver markings with darker green interveinal areas.

*Alocasia* 'Mandalay' differs from the commercial variety *Alocasia* 'Black Velvet' (unpatented) by having a leaf margin that is undulating to somewhat lobed and a leaf surface that is mostly flat to glabrous with a glossy sheen, whereas 'Black Velvet' has a leaf margin that is entire to slightly undulating and a leaf surface that is dull with a velvet appearance. Additionally, *Alocasia* 'Mandalay' has midrib and primary veins that protrude from the upper leaf surface, whereas 'Black Velvet' has midrib and primary veins that are recessed with the lamina of the leaf and convex interveinal areas, giving the leaf a textured appearance.

*Alocasia* 'Mandalay' differs from the commercial variety *Alocasia* 'Frydek' (unpatented) by having a shorter, more compact growing plant with more, shorter, ovate leaves, whereas 'Frydek' has a larger, more upright growing plant with fewer, larger, longer leaves. Additionally, *Alocasia* 'Mandalay' has dark green leaves that are shiny to glossy with more abundant silver venation, whereas 'Frydek' has green glistening textured leaves.

I claim:

1. A new and distinct variety of *Alocasia* plant named 'Mandalay' as described and shown herein.

* * * * *